(12) United States Patent
Hohjo et al.

(10) Patent No.: US 7,975,557 B2
(45) Date of Patent: Jul. 12, 2011

(54) MULTIPLE TESTING SYSTEM AND TESTING METHOD

(75) Inventors: Hiroshi Hohjo, Nagoya (JP); Hajime Ikuno, Seto (JP)

(73) Assignee: Kabushiki Kaisha Toyota Chuo Kenkyusho, Aichi-Gun (JP)

( * ) Notice: Subject to any disclaimer, the term of this patent is extended or adjusted under 35 U.S.C. 154(b) by 0 days.

(21) Appl. No.: 11/655,073

(22) Filed: Jan. 19, 2007

(65) Prior Publication Data
US 2007/0169563 A1 Jul. 26, 2007

(30) Foreign Application Priority Data
Jan. 24, 2006 (JP) .................. 2006-014886

(51) Int. Cl.
*G01N 19/08* (2006.01)
(52) U.S. Cl. ........................................ 73/799
(58) Field of Classification Search ............ 73/799, 73/805
See application file for complete search history.

(56) References Cited

U.S. PATENT DOCUMENTS

| 2,497,083 | A | * | 2/1950 | Hildebrand | 188/314 |
| 2,706,907 | A | * | 4/1955 | Cox | 73/809 |
| 2,836,060 | A | * | 5/1958 | Ciringione et al. | 73/805 |
| 3,199,672 | A | * | 8/1965 | Charland | 209/551 |
| 3,937,071 | A | * | 2/1976 | Slota et al. | 73/809 |
| 4,617,663 | A | * | 10/1986 | Lake et al. | 714/736 |
| 5,345,826 | A | * | 9/1994 | Strong | 73/826 |
| 6,189,385 | B1 | * | 2/2001 | Horiuchi et al. | 73/664 |
| 6,241,258 | B1 | * | 6/2001 | Roussel | 279/4.02 |
| 6,343,237 | B1 | * | 1/2002 | Rossow et al. | 700/83 |
| 6,598,480 | B2 | * | 7/2003 | Horiuchi et al. | 73/663 |
| 7,529,990 | B2 | * | 5/2009 | Haggerty | 714/724 |
| 7,610,578 | B1 | * | 10/2009 | Taillefer et al. | 717/124 |
| 2003/0074606 | A1 | * | 4/2003 | Boker | 714/42 |

FOREIGN PATENT DOCUMENTS

| JP | A-04-307350 | 10/1992 |
| JP | A 2003-75315 | 3/2003 |

OTHER PUBLICATIONS

JP 2006-014886 Notice of Reasons for Rejection, issued Jul. 21, 2009, with English-language translation.

* cited by examiner

*Primary Examiner* — Lisa M Caputo
*Assistant Examiner* — Octavia Davis
(74) *Attorney, Agent, or Firm* — Oliff & Berridge, PLC

(57) ABSTRACT

A multiple testing system has plural testing units which are disposed independently, and a single information processing device. The testing unit has a frame, a loading mechanism supported at the frame and applying a desired load quantity on a test body, and a detector detecting a load quantity applied on the test body. By multitasking control and with respect to the testing units, the information processing device carries out: feedback control processing for, on the basis of a detected load quantity, controlling the loading mechanism such that the detected load quantity becomes a predetermined target value; control processing at an abnormal situation when at least one of an abnormality of the test body, an abnormality of the testing unit, or an abnormality of a power source of the loading mechanism, is detected; and interface processing with an operator.

18 Claims, 8 Drawing Sheets

MULTIPLE TESTING SYSTEM AND TESTING METHOD

CROSS-REFERENCE TO RELATED APPLICATION

This application claims priority under 35 USC 119 from Japanese Patent Application No. 2006-014886, the disclosure of which is incorporated by reference herein.

BACKGROUND OF THE INVENTION

1. Field of the Invention

The present invention relates to a testing system and a testing method using a loading mechanism which applies a desired load quantity on a test body, and in particular, to a multiple testing system and a testing method which carry out testing in parallel by using plural testing units.

2. Description of the Related Art

Conventionally, evaluation of the fatigue life of the test body is carried out by loading on test bodies using a fatigue testing device. In recent years, there has been the demand to carry out evaluation of the fatigue life in an ultra-high cycle regime exceeding $10^7$ cycles. However, carrying out fatigue testing in an ultra-high cycle regime requires a long period of time.

In order to shorten the time required for fatigue testing, there is known a fatigue testing unit 110 such as that shown in FIG. 8 which effects control such that cyclic loading of a load on a test body is carried out at high speed. On the basis of an instruction from a computer 118, a servo amplifier 113 is controlled by a microcomputer 120 of a high speed controlling device 116, and a test waveform is outputted to a servo valve which carries out supply and adjustment of the flow rate of hydraulic fluid to a hydraulic actuator of a fatigue testing unit 112.

Because statistical evaluation is essential in order to evaluate the fatigue life in such an ultra-high cycle regime, a fatigue test must be carried out multiple times under the same load conditions, and the fatigue testing requires even more time.

In order to further shorten the time required for fatigue testing, carrying out testing in parallel by using plural fatigue testing units has been proposed. There is known a multiple fatigue testing unit system in which a single hydraulic power source is used in common for plural fatigue testing units, and the supply lines to the respective fatigue testing units are connected to an oil tank and a hydraulic pump which serve as the single hydraulic power source (Japanese Patent Application Laid-Open (JP-A) No. 2003-75315).

SUMMARY OF THE INVENTION

The present invention has been made in view of the above circumstances and provides a multiple testing system and a testing method.

According to an aspect of the invention, there is provided a multiple testing system having: a plurality of testing units which are disposed independently and each have a frame, a loading mechanism supported at the frame and applying a desired load quantity on a test body, and a detector detecting a load quantity applied on the test body; and a single information processing device which, by multitasking control and with respect to the plurality of testing units, carries out: feedback control processing for, on the basis of the load quantity detected by the detector, controlling the loading mechanism such that the detected load quantity becomes a predetermined target value; control processing at an abnormal situation when at least one of an abnormality of the test body, an abnormality of the testing unit, or an abnormality of a power source of the loading mechanism, is detected; and interface processing with an operator.

BRIEF DESCRIPTION OF THE DRAWINGS

Preferred embodiments of the present invention will be described in detail based on the following figures, wherein.

DETAILED DESCRIPTION OF THE INVENTION

A first embodiment of the present invention will be described hereinafter with reference to the drawings. In the first embodiment of the present invention, as an example, a case is described in which the present invention is applied to a fatigue testing system which uses a load serving as a load quantity which is loaded on a test body, a hydraulic actuator serving as a loading mechanism, and hydraulic pressure serving as a power source of the loading mechanism.

In the aforementioned JP-A No. 2003-75315, there is no disclosure relating to the processing method at the time when an abnormality occurs, such as a test body breaking at one fatigue testing device among the multiple fatigue testing devices. Accordingly, for example, if the supply of hydraulic fluid to a testing device at which an abnormality has occurred is stopped by an electromagnetic valve or the like, mutual interference occurs between the fatigue testing devices due to the sudden fluctuation in hydraulic pressure at the hydraulic power source, and the hydraulic pressure at the other fatigue testing devices, which are still continuing testing, fluctuates. Therefore, it can be thought that the problem will arise that stable load control cannot be carried out. Further, if no control processings are carried out at the time when a test body is damaged, there is the concern that control will become impossible, the hydraulic pressure will fluctuate abnormally, and damaging of other test bodies will occur or irreparable damage will be inflicted on the testing devices.

A multiple fatigue testing system in the first embodiment of the present invention, which, when an abnormality occurs, can carry out stable load control on the other fatigue testing units which are still continuing testing, will be described.

Figure 1:
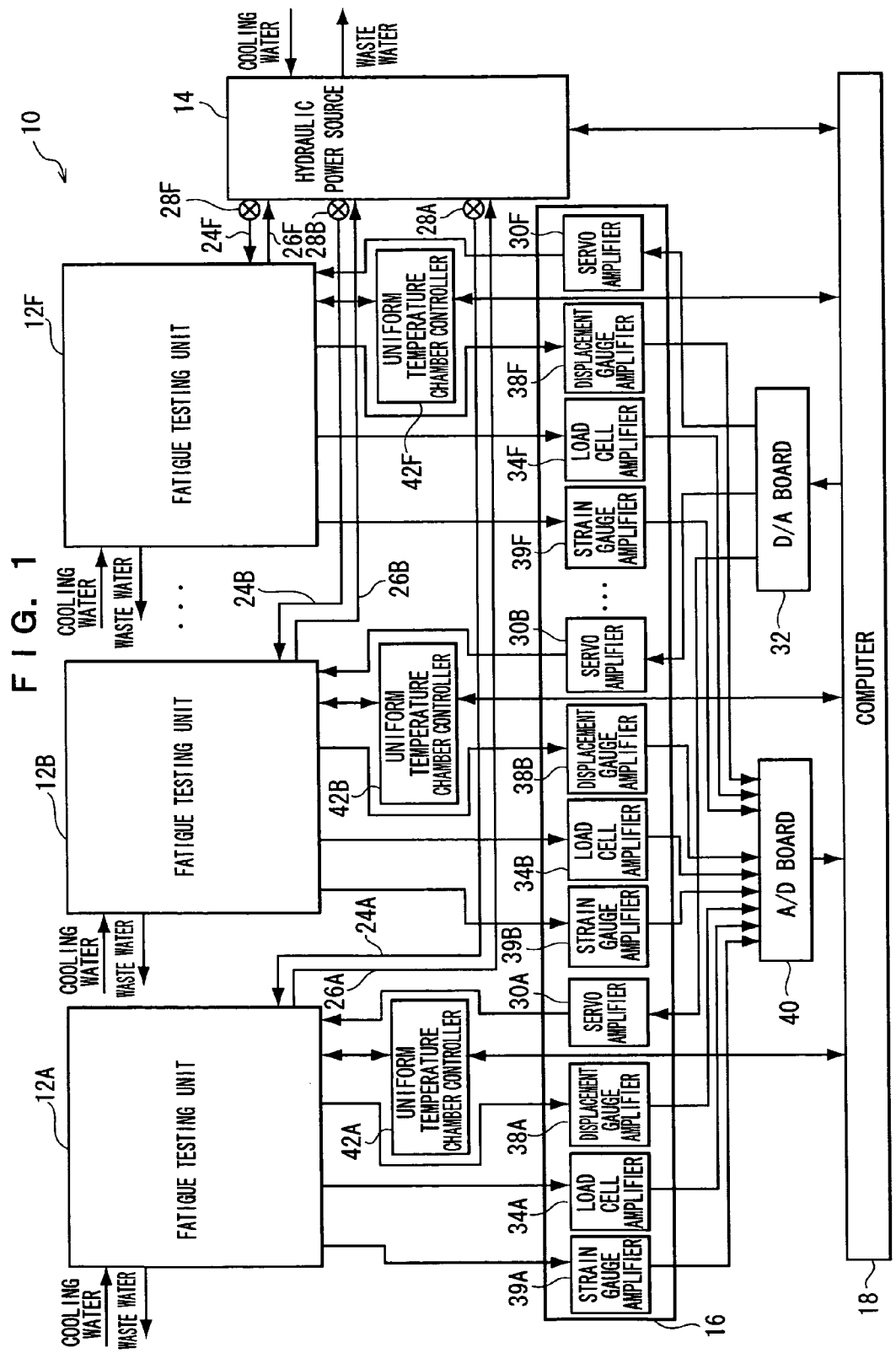
FIG. 1 is a function block diagram showing the structure of a multiple fatigue testing system relating to a first embodiment of the present invention.

As shown in FIG. 1, a multiple fatigue testing system 10 relating to the first embodiment of the present invention has, for example, six fatigue testing units 12A through 12F which are disposed independently, a hydraulic power source 14, supply lines 24A through 24F, and return lines 26A through 26F. The hydraulic power source 14 is formed from an oil tank (not shown) in which hydraulic fluid is stored, and a hydraulic pump (not shown) which pressurizes and supplies the hydraulic fluid. The supply lines 24A through 24F connect the hydraulic power source 14 and the fatigue testing units 12A through 12F in parallel, and supply the pressured hydraulic fluid. The return lines 26A through 26F return hydraulic fluid to the hydraulic power source 14. Note that the hydraulic power source 14 is used in common by the fatigue testing units 12A through 12F. Hydraulic fluid is independently supplied by the supply lines 24A through 24F to the fatigue testing units 12A through 12F respectively, and hydraulic fluid is independently returned by the return lines 26A through 26F respectively.

Electromagnetic valves 28A through 28F, which are for carrying out supplying or stopping of the hydraulic pressure by the respective supply lines 24A through 24F, are provided at the hydraulic power source 14.

An amplifier integrating stand 16 at which amplifiers are integrated, a computer 18 for controlling the fatigue testing units 12A through 12F, a multichannel D/A board 32, a multichannel A/D board 40, and uniform temperature chamber controllers 42A through 42F are provided at the multiple fatigue testing system 10. The multichannel D/A board 32 converts digital signals outputted from the computer 18, and outputs analog control command signals, which express load waveforms, to respective servo amplifiers 30A through 30F which will be described later. The multichannel A/D board 40 converts analog signals outputted from respective load cell amplifiers 34A through 34F which will be described later, and inputs digital signals to the computer 18. The uniform temperature chamber controllers 42A through 42F turn heaters of uniform temperature chambers, which will be described later, on and off by PID control.

The D/A board 32 has plural buffer regions which store the load waveform data which express the analog control command signals. The D/A board 32 repeats the following series of operations: when the D/A board 32 outputs a predetermined amount of the analog control command signals, the D/A board 32 sends, to the computer 18, an event signal requesting the next load waveform data, and, before completing output of the load waveform data stored in the buffer region previously, stores the next load waveform data in the next buffer region. In this way, the D/A board 32 has the function of continuously outputting of analog control command signals.

The servo amplifiers 30A through 30F, the load cell amplifiers 34A through 34F, displacement gauge amplifiers 38A through 38F, and strain gauge amplifiers 39A through 39F are provided at the amplifier integrating stand 16, independently for the respective fatigue testing units 12A through 12F. The servo amplifiers 30A through 30F amplify the analog control command signals, and output them to electrohydraulic servo valves which will be described later. The load cell amplifiers 34A through 34F amplify analog signals outputted from load cells. The displacement gauge amplifiers 38A through 38F amplify analog signals outputted from displacement gauges which will be described later. The strain gauge amplifiers 39A through 39F amplify analog signals outputted from strain gauges which will be described later. Further, power source switches (not shown) for turning the power sources of the above-described amplifiers on and off are provided at the amplifier integrating stand 16.

The A/D board 40 converts the analog signals outputted from the load cell amplifiers 34A through 34F, the displacement gauge amplifiers 38A through 38F, and the strain gauge amplifiers 39A through 39F respectively, and inputs digital signals to the computer 18.

Further, cooling water is sent-in and drained-out from the hydraulic power source 14 and the fatigue testing units 12A through 12F respectively.

A hard disk and a memory storing test data and a series of programs, which include a fatigue testing processing routine which will be described later, are provided at the computer 18. By operating in accordance with these programs, the computer 18 generates load waveform data for controlling the electrohydraulic servo valves of the respective fatigue testing units 12A through 12F, and outputs digital signals expressing the load waveform data to the D/A boards 32A through 32F respectively. Further, the computer 18 individually controls respective hydraulic actuators of the fatigue testing units 12A through 12F. The controlling of the respective fatigue testing units 12A through 12F is carried out in parallel by multitasking control. A large-capacity RAM is provided at the computer 18 in order to prevent use of a virtual memory using the hard disk where there is the risk that output of the digital signals expressing the load waveform data will stop.

Figure 2:
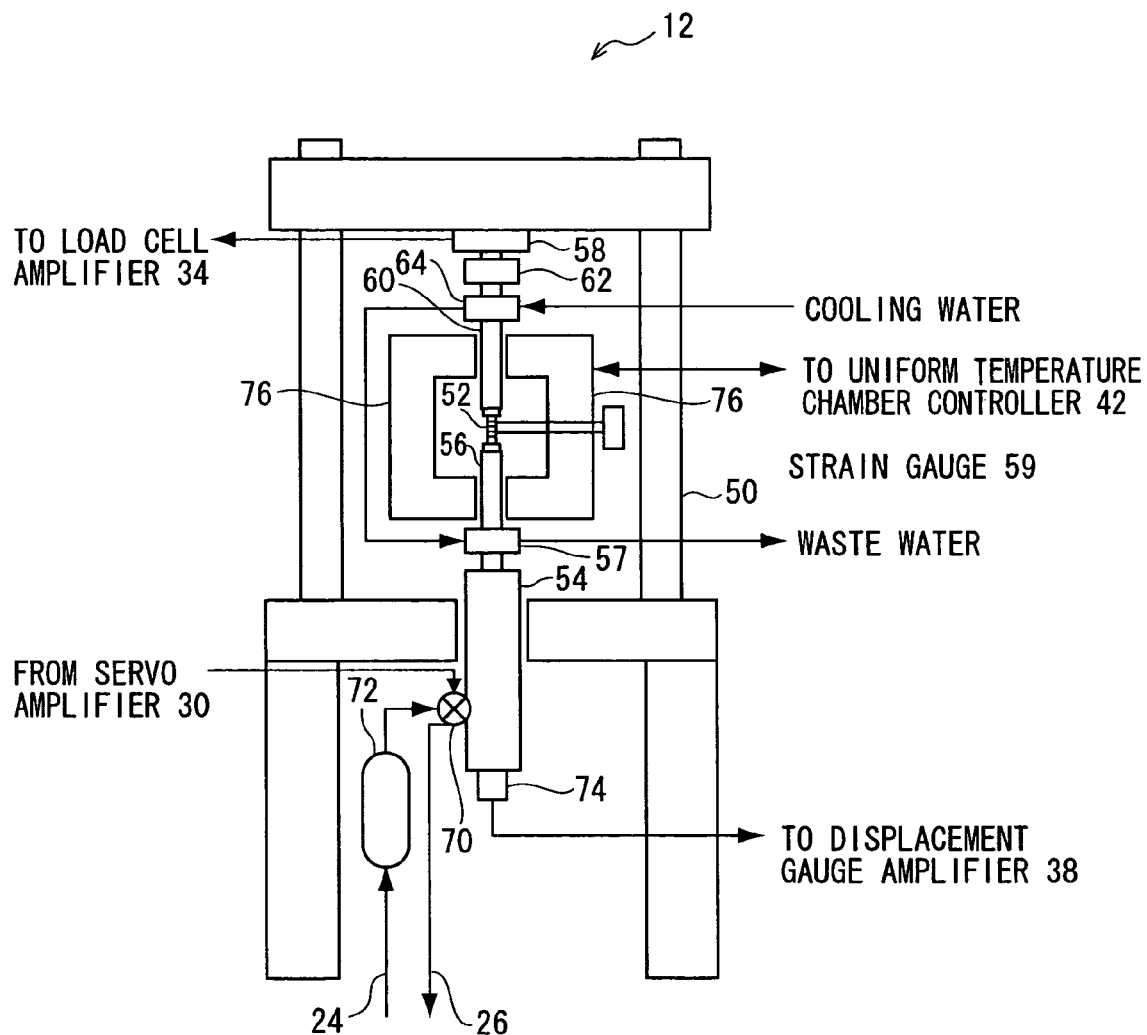
FIG. 2 is a schematic diagram showing the structure of a fatigue testing unit relating to the first embodiment of the present invention.

As shown in FIG. 2, each of the fatigue testing units 12A through 12F has a frame 50 and a hydraulic actuator 54. The frame 50 is formed in a rectangular shape on a floor via, for example, a vibration-proofing rubber. The hydraulic actuator 54 is supported at the frame 50 by being mounted to a lower beam of the frame 50, and applies load on a test body 52 by hydraulic pressure. The hydraulic actuator 54 is structured from a cylinder which is fixed to the lower beam of the frame 50, and a piston which is provided so as to partition the space within the cylinder into an upper chamber and a lower chamber.

A lower rod 56 is provided so as to extend upwardly from the piston of the hydraulic actuator 54 and pass through the cylinder. The test body 52 is set on the top end of the rod 56, and is fixed by chucks (not shown) provided at the top end of the rod 56.

A water jacket 57, for cooling the rod 56 by water at the time of carrying out high temperature testing, is provided at the rod 56.

A load cell 58, which detects the load applied on the test body 52, is mounted to an upper beam of the frame 50. A upper rod 60 is mounted to the bottom end of the load cell 58, and the test body 52 is set on at the bottom end of the rod 60. Chucks (not shown) which fix the test body 52 are provided at the bottom end of the rod 60. Further, the load cell 58 detects the load which is applied on the test body 52, and outputs an analog signal expressing the load to one of the load cell amplifiers 34A through 34F.

A strain gauge 59 is provided at the test body 52. The strain gauge 59 detects the strain of the test body 52, and outputs an analog signal expressing the detected strain to one of the strain gauge amplifiers 39A through 39F. For example, a contact-type extensometer which is adhered to the surface of the test body, such as a strain—electroresistance converting type foil strain gauge or a clip gauge or the like, or a non-contact-type extensometer such as a video camera or the like, can be used as the strain gauge 59.

An axial center adjusting device 62, which adjusts the position of the rod 60 in order to prevent eccentricity of the axis of the load applied to the test body, and a water jacket 64, which is for cooling the rod 60 by water at the time of carrying out high temperature testing, are provided at the rod 60. Further, for example, a spherical seat, which is structured by metal parts, is used in the axial center adjusting device 62, and, by adjusting attachment balance of bolts which are disposed around the spherical seat, the axial centers of the rod 56 and the rod 60 are adjusted such that eccentric load is not applied to the test body.

Cooling water is sent-into the water jacket 64 from the exterior, and this cooling water is further sent-into the water jacket 57, and waste water is discharged-out from the water jacket 57. These water jackets prevent the heat from a uniform temperature chamber 76 from affecting the load cell 58 and the hydraulic actuator 64 at the time of high temperature testing.

An electrohydraulic servo valve 70, which adjusts the supply of the hydraulic fluid to the hydraulic actuator 54 and the oil flow rate by an electromagnetic proportional valve, is provided at the portion where the hydraulic fluid is supplied to the hydraulic actuator 54 by the supply line 24A through 24F. Further, an accumulator 72, which is for decreasing the pulsation of the pressure of the hydraulic fluid supplied through the supply line 24, is provided at each of the supply lines 24A through 24F. One of the return lines 26A through 26F is connected to the electrohydraulic servo valve 70.

One of the servo amplifiers 30A through 30F is connected to the electrohydraulic servo valve 70. The electrohydraulic servo valve 70 adjusts the supply flow rate of the hydraulic fluid to the hydraulic actuator 54, on the basis of the analog signal which expresses the load waveform and which is inputted from one of the servo amplifiers 30A through 30F.

A displacement gauge 74, for detecting the displacement of the piston, is provided at the hydraulic actuator 54. An analog signal, which expresses the displacement of the piston, is outputted from the displacement gauge 74 to one of the displacement gauge amplifiers 38A through 38F.

The uniform temperature chamber 76, which is supported at the frame 50 so as to surround the test body 52 and which heats the test body 52 and maintains it at a constant and uniform temperature by turning a heater on and off or by controlling the current flowing to the heater, is provided at the fatigue testing unit 12. The uniform temperature chamber 76 is connected to one of the uniform temperature chamber controllers 42A through 42F. A signal, which expresses the temperature inside the uniform temperature chamber 76, is outputted from the computer 18 to the one uniform temperature chamber controller 42A through 42F, and the uniform temperature chamber controller 42A through 42F carries out temperature control by, for example, PID control.

In order to, accurately and at a high frequency, transfer a load which corresponds to the load waveform, the fixing of the above-described frame 50, and the rods 56, 60 which are mounted to the frame 50, and the hydraulic actuator 54, is structured by planar contact between all of the metal parts. This is because, if a low-rigidity part or the like made of resin or the like is interposed, the transfer of the load is not smooth. Further, if a projection or an inclined contact surface or the like exists on the transfer path of the load, it is a cause of offset of the axial center (eccentricity) and hinders transfer of the load amplitude.

The above-described frame 50, hydraulic actuator 54, rods 56, 60, water jackets 57, 64, load cell 58, strain gauge 59, axial center adjusting device 62, electrohydraulic servo valve 70, displacement gauge 74, and uniform temperature chamber 76, are individually provided in each of the plural fatigue testing units 12A through 12F.

Note that the computer 18 may have the general configuration and functions of a conventionally-known personal computer, and description of the general functions and structure of the computer 18 will be omitted.

Figure 3:
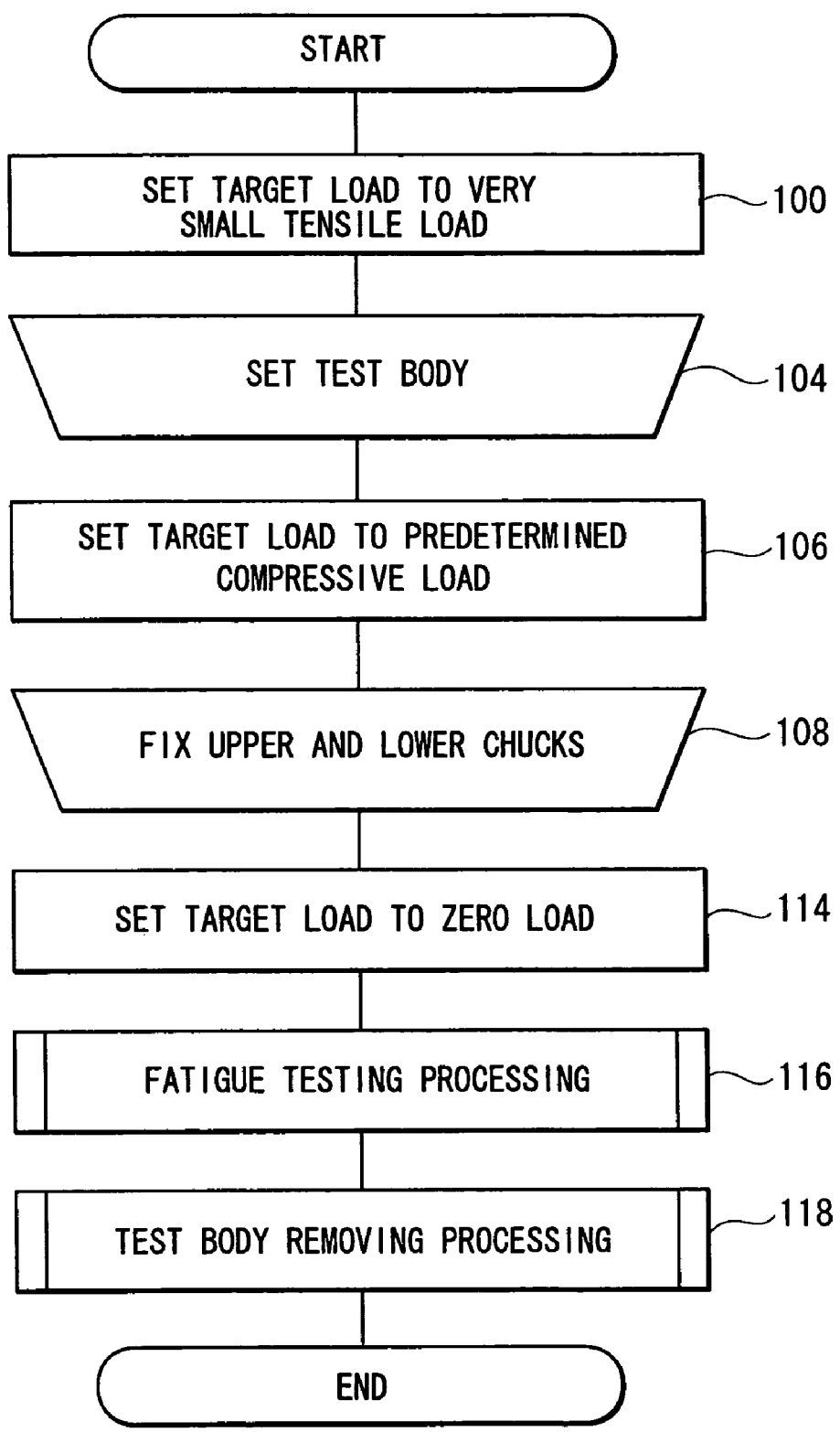
FIG. 3 is a flowchart showing the contents of a processing routine of a computer relating to the first embodiment of the present invention.

Operation relating to the first embodiment of the present invention will be described next. First, at the computer 18, the processing routine shown in FIG. 3 is executed in parallel by multitasking control with respect to the plural fatigue testing units. Note that the multitasking control is realized by a conventionally-known time division method or the like. Hereinafter, explanation will be given by using the fatigue testing processing routine for the fatigue testing unit 12A as an example.

First, the hydraulic power source 14 is started-up, the electromagnetic valves 28A through 28F are opened, and hydraulic fluid is supplied to all of the fatigue testing units 12A through 12F. The hydraulic fluid is supplied by the supply lines 24 to the hydraulic actuators 54 via the accumulators 72 and the electrohydraulic servo valves 70.

Then, in step 100, when the target load is set to a very small tensile load (e.g., +1 kgf) in a load controlling mode, the rod 56 at the lower portion descends to the lowest portion. In this state, in step 104, the test body 52 is set by an operator between the rod 60 at the upper portion and the rod 56 at the lower portion. In the first embodiment, explanation will be given by using, as an example, a fatigue test of a type in which the fixing portions of the test body 52 for fixing to the upper and lower rods 60, 56 are button-head-shaped, and compressive load is received at the both end surfaces of the button-head and tensile load is similarly received at the shoulder portions. Next, the routine moves on to step 106 where the set value of the target load is set to a predetermined compressive load (although it depends on the material properties, the dimensions and the testing temperature of the test body 52, it is a load which is so low as the test body 52 is not damaged, and, for example, is −30 kgf for a test body made of an aluminum alloy whose test portion has a circular cross-section of a diameter of 4 mm). When the set value of the target load is set to the predetermined compressive load, the rod 56 at the lower portion is raised, the test body 52 contacts the rod 60 and the rod 56 without any gaps therebetween, and the compressive load is applied. In this state, in step 108, the upper and lower chucks are fixed to the rods 56, 60 by the operator. Next, in step 114, the target load is set to zero load (0 kgf). In step 116, fatigue testing processing which will be described later is carried out. In step 118, test body removing processing is carried out, and the processing routine ends.

Note that, during the time from above-described step 100 to step 118, the load controlling mode is maintained as is without switching the control mode.

Figure 4:
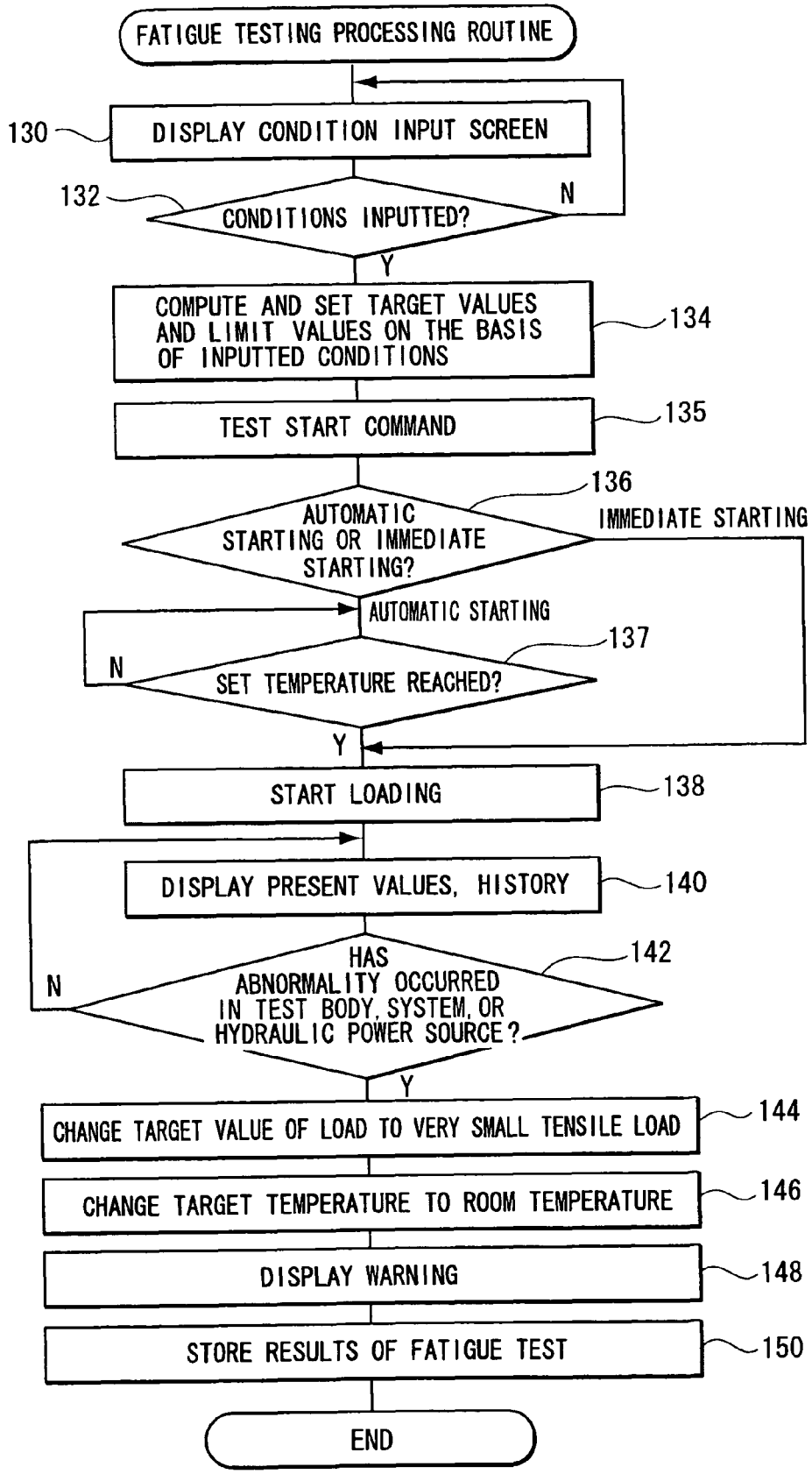
FIG. 4 is a flowchart showing the contents of a fatigue testing processing routine of the computer relating to the first embodiment of the present invention.

Next, the fatigue testing processing routine which realizes aforementioned step 116 will be described by using FIG. 4. First, in step 130, a condition input screen, which relates to the fatigue test to be carried out at the fatigue testing unit 12A, is displayed on a display (not shown) of the computer 18. In step 132, it is judged whether or not the fatigue test conditions are inputted. When an operator inputs, by a keyboard or a mouse (not shown) of the computer 18, the temperature of the test, or the average value and the amplitude of the stress applied on the test body 52, or the like as conditions relating to the fatigue test, the routine proceeds from step 132 to step 134. In step 134, on the basis of the inputted values, a target value of the temperature of the uniform temperature chamber 76, a target value of the load, a target value of the amplitude, upper and lower limit values for judging abnormality of the load, and a limit value for judging abnormality of the load amplitude, are computed, and the computed target values and limit values are set as the parameters of the fatigue test. Further, data expressing the target value of the temperature of the uniform temperature chamber 76 is outputted to the uniform temperature chamber controller 42, and is set as a parameter relating to the control of the uniform temperature chamber controller 42. Note that the temperature of the test body 52 and the temperature of the uniform temperature chamber 76 are related by a table which is provided in advance. The temperature of the uniform temperature chamber 76, which corresponds to the inputted temperature of the test, is determined on the basis of this table.

Next, in step 135, the operator inputs a command to start the test. In this command, it is possible to select automatic starting or immediate starting. In step 136, it is judged whether automatic starting or immediate starting is selected. If immediate starting is selected, the routine moves on to step 138, whereas if automatic starting is selected, the routine moves on to step 137.

In step 137, it is judged whether or not the temperature of the uniform temperature chamber 76 has reached a set value. When the heater of the uniform temperature chamber 76 is turned on by the uniform temperature chamber controller 42, and heating of the test body 52 is started, and the temperature of the uniform temperature chamber 76 reaches the set temperature of the uniform temperature chamber 76, the routine proceeds from step 137 to step 138. Note that, after the test body is set, when heating or cooling is to be carried out, it is desirable to select the load controlling mode. In this way, thermal stress can be prevented from occurring at the test body in the heating or cooling process. Further, the target load at this time is set to be, for example, 0 kgf. Moreover, if heating or cooling is carried out in a mode other than the load controlling mode, such as a displacement controlling mode which displaces the rod 56 or the like, avoiding the generation of thermal stress which is derived from the heating/cooling must be carried out by another method. For example, there is a method of varying the control set values other than the load so that the actual load is constant at zero. At this time as well, the control mode is not switched during the time from above-described step 100 to step 118.

In step 138, cyclic loading on the test body 52 is started. Note that it is possible to not start the cyclic loading on the test body 52 as soon as the set temperature is reached, and rather, to start the cyclic loading on the test body 52 after maintaining the state for a predetermined time period after the set temperature has been reached. The operator inputs a set value for this time period for maintaining the state to the computer 18 before inputting the automatic start command.

When the load start command is given from the computer 18, on the basis of the analog signal expressing the load waveform outputted from the D/A board 32, the electrohydraulic servo valve 70 adjusts the flow rate of the hydraulic fluid supplied to the hydraulic actuator 54. The hydraulic actuator 54 applies a load on the test body 52 by the supplied hydraulic pressure, and applies cyclic loading of a predetermined amplitude around a set average load on the test body 52 at a predetermined frequency. Note that the hydraulic pressure is constant for all of the fatigue testing units 12A through 12F.

Then, in step 140, the present values and the waveforms of the load detected by the load cell 58 and the piston displacement detected by the displacement gauge 74, and the history of the peak value of the piston displacement, and the history of the peak value of the applied load, are displayed on the display of the computer 18 every given time. In step 142, it is judged whether or not an abnormality of the test body 52, a system abnormality of the fatigue testing unit 12A, or an abnormality of the hydraulic power source 14 has occurred. In this judgment, the upper and lower peak values of the displacement of the piston and the upper and lower peak values of the applied load monitored on the basis of the digital signal, which is inputted from the displacement gauge amplifier 38A via the A/D board 40 and expresses the displacement of the piston of the hydraulic actuator 54, and the digital signal, which is inputted from the load cell amplifier 34A via the A/D board 40 and expresses the load. When these upper and lower peak values are within the limit values set in step 104, the routine returns to step 140. If the upper and lower peak values exceed the limit values, it is judged that an abnormality including fracture of the test body 52, a system abnormality of the fatigue testing unit 12A, or an abnormality of the hydraulic power source 14 has occurred, and the routine moves on to step 144. Note that, at this time, it is specified whether or not there is an abnormality of the test body 52, whether or not there is a system abnormality of the fatigue testing unit 12A, or whether or not there is an abnormality of the hydraulic power source 14. At this time, a case in which the load amplitude is smaller than the limit value is judged to be abnormal.

Then, in step 144, supposing also a case in which the test body 52 is not broken, the target load is changed such that tensile stress, which is very small and constant and sufficiently lower than the residual strength of the test body 52, is applied. For example, in the case of a test body made of an aluminum alloy which has a circular cross-section of a diameter of 4 mm, the target load is changed so that the tensile load is +1 kgf and is a constant value. In this way, the piston of the hydraulic actuator 54 moves in the direction in which a very small tensile load is applied on the test body 52. If the test body 52 is completely separation-broken, the piston of the hydraulic actuator 54 moves to the lowest position, and the fracture surfaces of the specimen 52 are protected. Note that the electromagnetic valve 28A holds still open, and the state in which the hydraulic fluid is supplied from the hydraulic power source 14 is maintained.

Other than fracture of the test body 52, a decrease in rigidity due to the generation and progression of cracks is an abnormality of the test body 52. Further, as system abnormalities of the fatigue testing unit 12, there are abnormalities in load, displacement, and strain, and an abnormality in the temperature of the uniform temperature chamber. Further, there are an abnormality in hydraulic pressure and an abnormality in oil temperature as abnormalities of the hydraulic power source 14. The aforementioned abnormalities of the test body 52 are judged from the measured value of the load quantity, but may be judged by separately using a sensor for detection.

The peak values and the amplitude values of the values which the load cell 58, the strain gauge 59, and the displacement gauge 74 detect, are monitored each predetermined period of time. In a case in which a limit value which is set in advance is exceeded, an abnormality of over load or degradation of amplitude is detected. Further, in the load controlling mode, in a case in which a predetermined target load is not applied, fracture of or a decrease in the rigidity of the test body 52 is detected. In the displacement controlling mode and the strain controlling mode, in a case in which the load suddenly decreases and the load amplitude becomes zero and constant, fracture of or a decrease in the rigidity of the test body 52 also is detected. In cases of the aforementioned abnormalities, the target load is changed such that a very small tensile load is applied.

Further, in a case in which a temperature abnormality is detected by a temperature sensor provided within the uniform temperature chamber 76, the target temperature is changed to, for example, room temperature (20° C.), and the target load is changed such that a very small tensile load is applied.

Then, in step 146, the target temperature of the uniform temperature chamber 76 is changed to, for example, a temperature equal to room temperature, in order to maintain the operating state of the uniform temperature chamber 76. In next step 148, a warning is displayed on the display of the computer 18, and the operator is informed that an abnormality has occurred at the fatigue testing unit 12A. In step 150, conditions relating to the fatigue test, histories of various types of values, the time until the abnormality occurred, the number of cycles, and the load waveform at the time when the abnormality occurred are stored as results relating to the fatigue test, and the fatigue testing processing routine ends.

The above-described fatigue testing processing routine is executed continuously by multitasking control for the other fatigue testing units 12B through 12F. At this time, even if an abnormality including fracture of the test body 52 occurs at the fatigue testing unit 12A, the electromagnetic valve 28A is not closed, and the hydraulic fluid continues to be supplied. In this way, fluctuations in hydraulic pressure due to closing the electromagnetic valve 28A do not arise, and therefore, mutual interference due to fluctuations in the hydraulic pressure does not arise at the other fatigue testing units 12B through 12F.

Further, because of maintaining the operating state of the uniform temperature chamber 76 of the fatigue testing unit 12A, noise does not get interference on the electric signals relating to the control of the present system, such as the signals for controlling the temperatures of the uniform temperature chambers 76 of the other fatigue testing units 12B through 12F, the output signals from the load cell 58, the displacement gauge 74 and the strain gauge 59, the signals for controlling the load waveforms, and the like. Therefore, stable load waveform control and temperature control can be carried out.

When fatigue testing is being carried out at the respective fatigue testing units 12A through 12F, the present values, the waveforms, and the histories are displayed on the display of the computer 18. At this time, display can be switched between a screen which displays the states of all of the fatigue testing units 12A through 12F together on one screen, and a screen which displays details of any of the fatigue testing units 12A through 12F. The display screen is switched by the operator clicking the mouse, or the like.

As described above, at the time when load waveform data is outputted to the D/A board 32 on the basis of the target load, the load waveform data is updated at a predetermined time interval on the basis of output from the load cell 58.

The D/A board 32 has the function of outputting a control command signal of a fixed value and maintaining it, in a case in which the next load waveform data is not stored in the buffer region at the time of completion of output of the analog control command signal. In this way, even if the computer 18 hangs-up, the respective fatigue testing units 12 are maintained in a stable state without the output of the analog control command signal, which expresses the load waveform, from the D/A board 32 becoming an abnormality.

In the updating of the load waveform data, in addition to conventional feedback control, the target load is corrected each predetermined time period on the basis of the error between the target load and the load sensed by the load cell 58. This correction is carried out gradually in plural steps on the error amount. In this way, hunting of the control is suppressed, and smooth control is possible. With conventional PID control, a control deviation remains, but in the multiple fatigue testing system relating to the present embodiment, the target load is corrected by directly reflecting the error. Therefore, stable and highly-accurate control is carried out under a broad range of test conditions.

Further, the computer 18 has a function which, in a case in which output of the load waveform from the D/A board 32 stops, senses this and automatically restarts output of the load waveform. For example, the computer 18 senses a load waveform data request event from the D/A board 32, and carries out control. If over load is applied to the CPU in an operation other than testing control, or the like, and in the unlikely event that there is a failure to sense this interruption and output of the analog control command signal is stopped, the updating of the load waveform data from the D/A board 32 is carried out on the basis of the last load waveform data just before the stoppage, and control is restarted.

In this way, even in the unlikely event in which output of the load waveform stops, restoring can be carried out automatically, and all of the fatigue testing units 12 can be normally operated very stably over a long period of time.

The program for executing the processing routine shown in FIG. 3 which the computer 18 executes, has a program module for updating the load waveform data. This program module controls such that the sum of a time period $t2$, which is required for storage of the next load waveform data, and a time period $t3$, which is required for the processing whose required time is the longest among the processings which are carried out continuously and cannot sense an interruption event signal, is shorter than a time period $t1$, which is since a predetermined amount of the analog control command signal is outputted and the next load waveform data is requested until completion of the output of the analog control command signal expressing the load waveform data which was stored previously, (i.e., $t1>t2+t3$), so that the next load waveform data is stored in a buffer region of the D/A board 32 before output of the analog control command signal is completed. In this way, processing which causes the analog control command signal to be output continuously is carried out by multitasking control with respect to each of the plural fatigue testing units 12. Namely, in order to carry out multitasking control without stopping the testing units, the execution time of the program is made to be short such that updating of the data of the D/A board 32 can be carried out continuously, and the control of the load waveform can be carried out continuously without stoppage. Or, an interruption sensing function may be provided at the program so that a data request interruption from the D/A board 32 can be detected within a predetermined processing time.

Control unit identifying variables, which are used in identifying the fatigue testing units 12 at the time when the various types of control of the respective fatigue testing units 12 are carried out, and interface unit identifying variables, which are used in identifying the fatigue testing unit 12 in processing for accessing a specific fatigue testing unit 12 at the time when an operator carries out setting of test conditions or confirming of the status of a test by using an external inputting device such as a keyboard or a mouse or the like, are provided distinctly as individual variables in the above-described program. In this way, confusing of the fatigue testing units 12 between the control of the respective fatigue testing units 12 which the program executes automatically by interruption processing, and the process of accessing a specific fatigue testing unit 12 by operation of an operator from the exterior, is eliminated, and erroneous operation at the multiple fatigue testing system 10 can be prevented.

Further, in the above description, the control unit identifying variables are local variables which, when used within an individual program module which has been subdivided, are effective only within that module. In this way, even in a case in which control of another program module interrupts and is executed during the execution of an individual program due to multitasking control, confusion as to the objective fatigue testing unit 12 does not arise, and the multiple fatigue testing system is operated stably.

Further, the interface unit identifying variables are global variables which can be used in common at the individual program modules which have been subdivided. Or, the interface unit identifying variables which are global variables are re-defined and used as local variables within an individual program module. Moreover, the values of the global variables are changed only when the operator carries out input which intentionally changes the unit to be accessed, and in all other cases, changing is not carried out at will at the program side. In this way, the fatigue testing unit which the operator accesses is specified, and erroneous operation is avoided.

Figure 5:
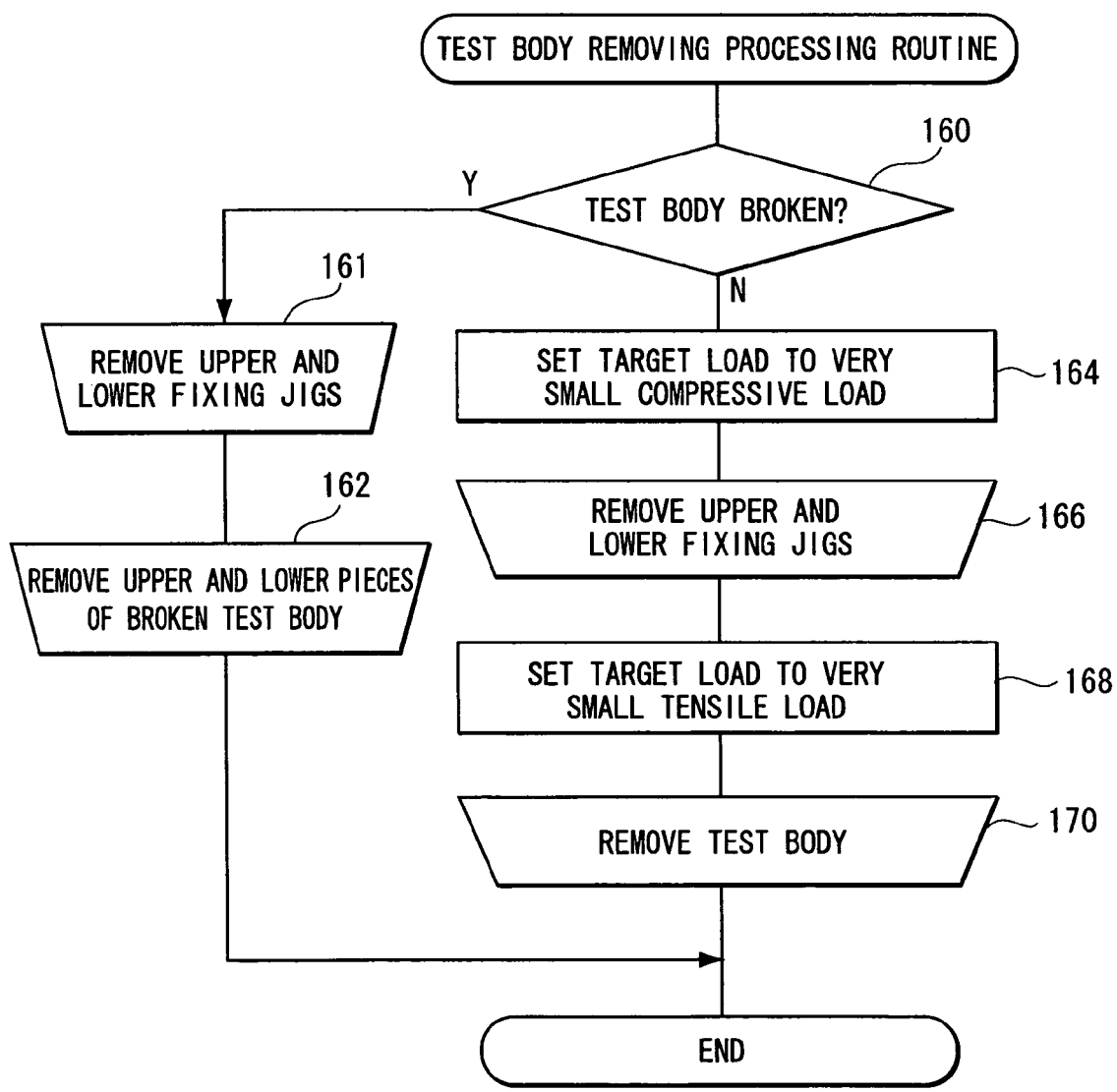
FIG. 5 is a flowchart showing the contents of a test body removing processing routine of the computer relating to the first embodiment of the present invention.

Next, the test body removing processing routine for realizing above-described step 118 will be described by using FIG. 5. First, in step 160, it is judged whether or not the test body 52 has broken. If it was judged in previously-described step 142 that the test body 52 is separation-broken, in the state in which the lower rod 56 is stopped at the lowest limit position in the movable range due to the very small tensile load of above-described step 144, the operator removes the upper and lower fixing jigs in step 161, and, in step 162, removes the upper and lower portions of the test body, and the test body removing routine ends.

On the other hand, if the test body 52 has not completely broken, in step 164, the target load is set to a very small compressive load (e.g., −1 kgf). In step 166, the operator removes the upper and lower fixing jigs. In step 168, the target load is set to a very small tensile load (e.g., +1 kgf). In the state in which the lower rod 56 is lowered to the lowest limit position, in step 170, the operator removes the test body 52, and the test body removing processing routine ends.

By the above-described routine for mounting the test body and test body removing processing routine, the test body 52 can be removed without applying over load, with the load controlling mode remaining as is and without switching the control mode since mounting the test body 52 to at least one of the fatigue testing units 12 until removing the test bodies 52 from all of the fatigue testing units 12. On the other hand, in the conventional techniques, the mounting of the test body is carried out in a combined mode of load controlling and displacement controlling, and thereafter, at the time of starting test, the control mode is switched to the load controlling mode for testing. The combined mode of load controlling and displacement controlling is a mode which carries out displacement control such that the load does not exceed a given, fixed value, and has the function of preventing over load from being applied to the test body at times of mounting and removing the test body. However, after the mounting of the test body is completed, the mode must be switched to the load control mode for testing, and therefore, there is the risk that erroneous operation due to electromagnetic noise or abnormal vibration due to imperfect gain adjustment may arise. For example, the switching of the control mode is carried out by selecting the output of any of the load cell 58, the strain gauge 59 and the displacement gauge 74 as the input used in feedback control processing. At this time, because switching is carried out at a control sensitivity which is appropriate for each control mode, if the control sensitivity before and after the switching differs greatly, the piston of the hydraulic actuator 54 is suddenly displaced due to the switching, and an over load is applied to the test body 52. In order to prevent this, the control sensitivity is adjusted to the appropriate control sensitivity in advance. However, at this time, abnormal vibration of the piston may occur, and emergency stoppage must be carried out.

As described above, in accordance with the multiple fatigue testing system relating to the first embodiment of the present invention, by carrying out fatigue testing simultaneously at each of the plural fatigue testing units, the time required for fatigue testing can be shortened. Further, the plural fatigue testing units are disposed individually, and, when it is judged, on the basis of the load detected by the load cell, the displacement detected by the displacement gauge and the strain detected by the strain gauge of a fatigue testing unit, that an abnormality including fracture of a test body has occurred at a fatigue testing unit, the electrohydraulic servo valve is controlled and the state in which hydraulic fluid is supplied to the fatigue testing unit at which the abnormality has occurred is maintained such that mutual interference due to fluctuations in hydraulic pressure does not arise among the plural fatigue testing units, and further, by controlling the electrohydraulic servo valve such that a very small tensile load is applied on the test body by the hydraulic actuator, the occurrence of sudden fluctuations in hydraulic pressure can be prevented. Therefore, stable load control can be carried out with respect to the other fatigue testing units which are in the midst of continuing testing, and, even though there are multiple fatigue testing units, testing can be continued stably over a long period of time.

By using the single hydraulic power source and the single computer in common at the plural fatigue testing units, costs required by the multiple fatigue testing system can be suppressed.

When a test body breaks, the electrohydraulic servo valve is controlled in the direction in which a tensile load is applied on the test body by the hydraulic actuator. The fracture surfaces of the test body can thereby be protected.

Fatigue testing can be carried out in a state in which the test body is heated to a desired temperature by the uniform temperature chamber. Further, when an abnormality arises at the fatigue testing unit, the uniform temperature chamber is controlled so as to maintain the operating state of the uniform temperature chamber. Therefore, stable load waveform control and temperature control can be carried out on the other fatigue testing units which are still continuing testing.

By controlling the respective plural fatigue testing units by multitasking control at the computer, the time of the operator spent for the fatigue testing can be shortened even more.

The load waveform data is generated by the computer, a signal expressing the load waveform data is inputted, and the electrohydraulic servo valve is controlled. In this way, the electrohydraulic servo valve can be controlled highly accurately, and the fatigue strength property of the test body can be evaluated highly accurately.

By clicking on the mouse of the computer, or the like, display is switched between a screen, which collectively displays information of the plural fatigue testing units, and a screen, which displays detailed information of any of the plural fatigue testing units. In this way, the convenience of use for the operator can be improved.

The loading is started automatically after the temperature of the test body reaches a target temperature. The burden on the operator can thereby be reduced.

The frame of the fatigue testing unit is supported by vibration-proofing rubber. In this way, effects of the vibrations of the plural fatigue testing units on one another can be eliminated.

When the computer hangs-up, a control command signal of a fixed value is outputted from the D/A board and maintained. In this way, the respective fatigue testing units can be maintained in a stable state.

The computer is provided with a function which, when output of the load waveform by the D/A board is stopped, controls the D/A board so as to cause automatic re-starting of output of the load waveform. In this way, even in the unlikely event in which output of the load waveform stops, restoring is carried out automatically, and the multiple fatigue testing system can be normally operated very stably over a long period of time.

Note that, as an example, description is given above of a case in which fatigue testing is carried out in accordance with the load controlling mode. However, creep testing may be carried out in accordance with the load controlling mode. Or, tension testing, bending testing, or relaxation testing may be carried out in accordance with the displacement controlling mode or the strain controlling mode. Further, thermo-mechanical fatigue testing may be carried out by controlling the temperature under the strain controlling mode and applying heating-cooling thermal cycles.

A second embodiment will be described next. Portions which are structures and operations similar to those of the first embodiment are denoted by the same reference numerals, and detailed description thereof is omitted.

The second embodiment differs from the first embodiment with respect to the point that the test body 52 is fixed by screws in the second embodiment. Further, screws are formed in upper and lower portions of the test body 52, and nuts for fixing are disposed at the upper and lower screw portions.

Because the other structures are similar to those of the first embodiment, description thereof will be omitted.

Figure 6:
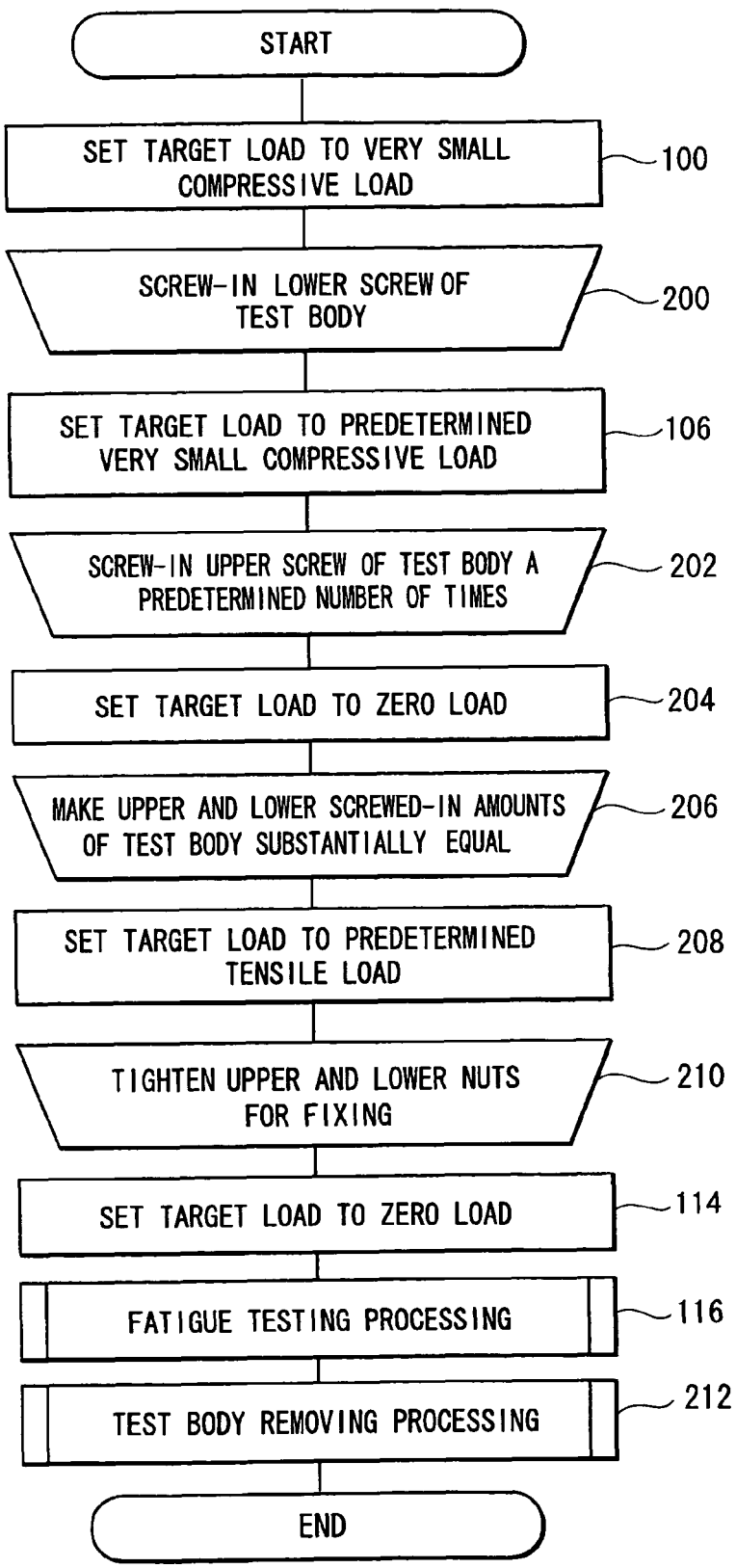
FIG. 6 is a flowchart showing the contents of a processing routine of a computer relating to a second embodiment of the present invention.

Operation of the second embodiment will be described next. First, the processing routine shown in FIG. 6 is executed in parallel by multitasking control at the computer 18. Hereinafter, the fatigue testing processing routine for the fatigue testing unit 12A will be described as an example.

First, in step 100, when the target load is set to a very small tensile load (e.g., +1 kgf) in the load controlling mode, the lower rod 56 is lowered to the lowest position. In this state, in step 200, the test body 52 is placed by an operator between the upper rod 60 and the lower rod 56, and screws at the lower portion of the test body 52 are screwed-in a predetermined number of rotations into a holder which is mounted to the top surface of the lower rod 56. Next, the routine moves on to step 106 where the target load is set to a predetermined compressive load (e.g., −1 kgf for a test body made of an aluminum alloy whose test portion has a circular cross-section of a diameter of 4 mm).

Then, the lower rod 56 is raised, and, in the state in which the test body 52 contacts the rod 60 and the rod 56 without any gaps therebetween, in step 202, the test body 52 is rotated and screws at the upper portion of the test body 52 are screwed-in a predetermined number of rotations into a holder which is mounted to the upper rod 60. At this time, the screws cannot be screwed in if the phases of the female screws at the upper holder and the phases of the male screws at the upper portion of the test body 52 do not match one another. However, this phase matching can be carried out by the operator grasping the upper rod 60 with his/her hand, and applying a very small load thereto in the vertical direction, and slightly raising or lowering the lower rod 56. While applying rotational force to the test body 52, the screws can be screwed-in easily when the phases match. When the screws can be screwed-in a bit, the routine moves on to step 204 where the target load is set to zero load, and the screwing-in thereafter is facilitated. In step 206, the test body 52 is screwed-in by the operator. When the upper and lower screwed-in amounts of the test body 52 are substantially equal, in step 208, the target load is set to a predetermined tensile load (a load which is so low as the test body 52 is not damaged, and, for example, is +30 kgf for a test body made of an aluminum alloy whose test portion has a circular cross-section of a diameter of 4 mm).

Then, in step 210, nuts for fixing, which are disposed at the upper and lower screw portions of the test body 52, are rotated by the operator, and tightened into the upper and lower holders with a predetermined torque so as to fix the test body 52 to the holders without any gaps. The routine moves on to step 114 where the target load is set to zero load (0 kgf). In step 116, the above-described fatigue testing processing is carried out. In step 212, test body removing processing is carried out, and the processing routine ends.

Figure 7:
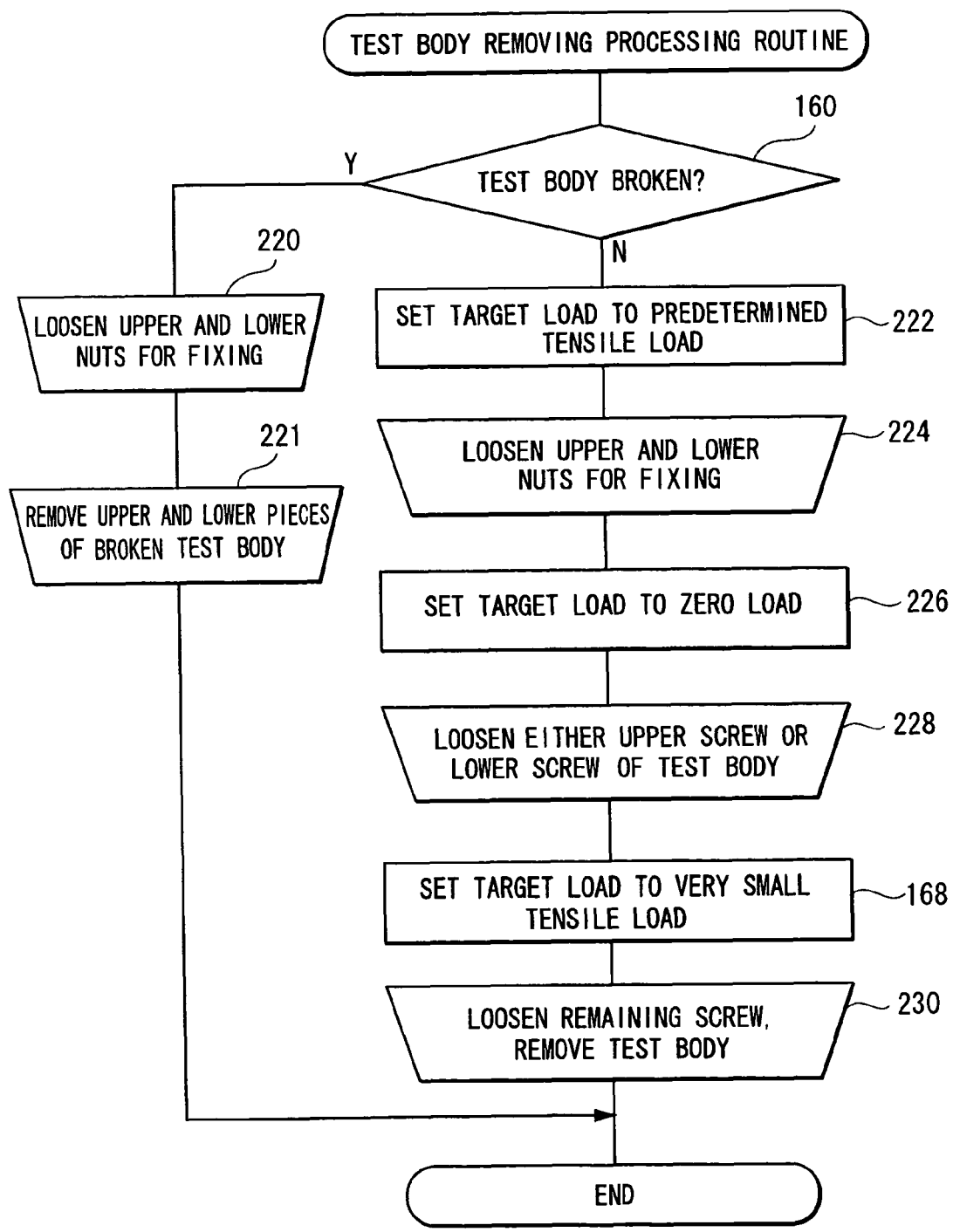
FIG. 7 is a flowchart showing the contents of a test body removing processing routine of the computer relating to the second embodiment of the present invention.
Figure 8:
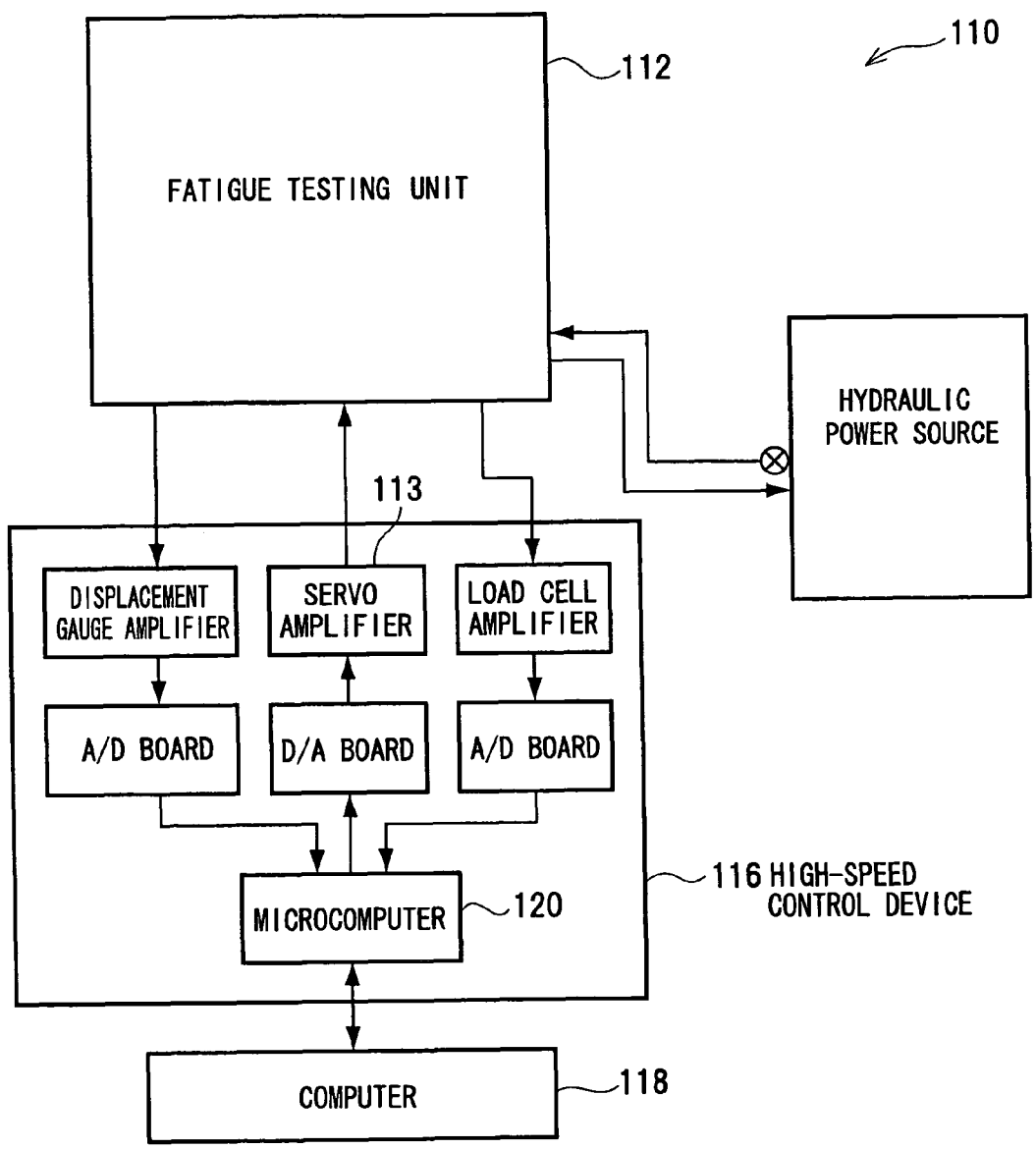
FIG. 8 is a function block diagram showing the structure of a conventional fatigue testing unit.

A test body removing processing routine, which is for realizing the test body removing processing of above-described step 212, will be described next by using FIG. 7.

First, in step 160, it is judged whether or not the test body 52 has broken. In a case in which it was judged in previously-described step 142 that the test body 52 is completely separation-broken, in a state in which the lower rod 56 is stopped at the lowest limit position within the movable range due to the very small tensile load of above-described step 144, the operator loosens the upper and lower nuts for fixing in step 220. In step 221, the operator removes the upper and lower portions of the test body 52, and the test body removing processing routine ends.

On the other hand, if it is judged in step 160 that the test body 52 has not broken, in step 222, the target load is set to a predetermined tensile load (e.g., +10 kgf for a test body made of an aluminum alloy whose test portion has a circular cross-section of a diameter of 4 mm). In the state in which the tensile load is applied to the test body 52, in step 224, the operator loosens the upper and lower nuts for fixing. In step 226, the target load is set to zero load, and the test body 52 can be screwed-into either of the upper and lower holders.

Then, in step 228, the operator completely removes the screws at the side opposite the one of the upper and lower portion of the test body 52 which was screwed-in as described above. The routine moves on to step 168 where the target load is set to a very small tensile load. Then, in the state in which the lower rod 56 is lowered to the lowest limit position, in step 230, the operator removes the screws at the side opposite the screws which were removed previously, and removes the test body 52, and the test body removing processing routine ends.

As described above, in accordance with the multiple fatigue testing system relating to the second embodiment, when mounting a test body which is to be fixed by screws, the test body is mounted with the load controlling mode set as is, without switching the control mode. In this way, effects on the operations of the other fatigue testing units due to switching of the control mode can be prevented from arising. Therefore, even though there are multiple fatigue testing units, they can continue testing stably over a long period of time.

When removing the test body as well, the test body can be removed without applying an over load to the test body, with the load controlling mode set as is and without switching the control mode.

Embodiments of the present invention have been described above, but it will be clear to those skilled in the art that the present invention is not limited to the above-described embodiments.

In accordance with a first aspect of the present invention, there is provided a multiple testing system having: a plurality of testing units which are disposed independently and each have a frame, a loading mechanism supported at the frame and applying a desired load quantity on a test body, and a detector detecting a load quantity applied on the test body; and a single information processing device which, by multitasking control and with respect to the plurality of testing units, carries out: feedback control processing for, on the basis of the load quantity detected by the detector, controlling the loading mechanism such that the detected load quantity becomes a predetermined target value; control processing at an abnormal situation when at least one of an abnormality of the test body, an abnormality of the testing units, or an abnormality of a power source of the loading mechanism, is detected; and interface processing with an operator.

Here, the load quantity means a mechanical quantity such as load, displacement, strain or the like, or temperature, or the like.

In accordance with the multiple testing system relating to the above-described aspect, for the plural testing units, the single information processing device controls the loading mechanisms by multitasking control. At each of the plural testing units which are disposed independently, a desired load quantity is applied to the test body by the loading mechanism, and the load quantity applied on the test body is detected by the detector.

At this time, the single information processing device carries out by multitasking control: feedback control processing which, on the basis of the load quantity detected by the detector, controls the loading mechanism such that the detected load quantity becomes the predetermined target value; control processing at an abnormal time when at least one of the abnormality of the test body, the abnormality of the testing unit, or the abnormality of the power source of the loading mechanism, is detected; and interface processing with the operator (processings such as inputting test conditions, instructing the start of testing, confirming the intermediate progress of testing, confirming the operating status of the system, instructing ending of testing, processings relating to mounting and removing the test body, storing test data such as test results, load history and the like, and the like).

In accordance with the above-described system, by carrying out testing by simultaneous progress by the plural testing units, the time required for testing can be shortened, and, even when there are multiple testing units, all of the testing units can continue testing stably over a long period of time. By providing the single information processing device and using it in common at the plural testing units, the costs required for the multiple testing system can be greatly suppressed. Further, because the operator can carry out operating of all of the testing units from the single information processing device, the number of work processes can be greatly reduced.

The respective loading mechanisms of the plural testing units relating to the above-described aspect may be connected in parallel to the single power source. In this way, the costs required for the multiple testing system can be suppressed even more. There is also the advantage that maintenance of the power source is made easy.

The control processing by the information processing unit at an abnormal time relating to the above-described aspect may effect fixed value control by changing the target value to a fixed value which is determined in advance for each cause of abnormality, when at least one of the abnormality of the test body, the abnormality of the testing unit, or the abnormality of the power source of the loading mechanism is detected. In this way, operation of only the testing unit at which the abnormality has arisen can be stopped safely, without affecting control of the other testing units at all.

The loading mechanism of the testing unit relating to the above-described aspect may load one or more of a desired load, displacement, strain, or temperature on the test body. The feedback processing may have one or more control modes among a displacement controlling mode which controls displacement of the test body, a load controlling mode which controls a load applied on the test body, a load—displacement combination controlling mode which simultaneously controls the load and the displacement (a mode which controls the displacement so that the load does not exceed a given, fixed value, or a mode which is the opposite thereof), a strain controlling mode controlling strain caused at the test body, a temperature controlling mode controlling the temperature of the test body, or a temperature—mechanical quantity combination controlling mode which simultaneously controls temperature and any of load, displacement or strain (a mode which controls a mechanical quantity while maintaining the temperature at a given, fixed value, or a mode which is the opposite thereof). From the start of mounting of the test body to at least one of the testing units until removal of the test bodies from all of the testing units, control may be carried out in accordance with the same control mode without switching the control mode. In this way, operations of the other testing units can be prevented from being affected by switching of the control mode.

The information processing device relating to the above-described aspect may further carry out processing at a time of replacement which, at the time of removing the test body and at the time of mounting the test body, effects control by changing only the target value in the same control mode without switching the control mode. In this way, because the operations of the other testing units are not affected, the removal and mounting of the test body can be carried out while the operation of the other testing units continues as is.

The multiple testing system relating to the above-described aspect may further have a multichannel D/A board which outputs control command signals for controlling the loading mechanisms to the respective plurality of testing units, and the D/A board may have a plurality of buffer regions storing output data expressing the control command signals, and may have a function of continuously carrying out output of the control command signals by repeating a series of operations of, when the D/A board outputs a predetermined amount of the control command signals, the D/A board sends an event signal requesting next output data to the information processing device, and, before output of output data stored in an active buffer region previously is completed, the D/A board stores the next output data in a next buffer region, and the D/A board may further have a function of outputting a fixed control command signal and maintaining it, in a case in which the next output data is not stored in the next buffer region when output of the control command signals is completed. In this way, at the time when the information processing device hangs-up, the fixed control command signal is outputted from the D/A board, and the respective testing units can be maintained in stable states.

Note that, if output data is stored in the final buffer region and there is no next buffer region which is free, the leading buffer region may correspond to the next buffer region.

Further, in the above-described structure, the information processing device may effect control such that a sum of a time period $t2$, which is required for storage of the next output data, and a time period $t3$, which is required for a processing whose required time is longest among processings which are carried out continuously and cannot sense the event signal, is shorter than a time period $t1$, which is since the event signal is sent from the D/A board until completion of the output of the control command signals expressed by the output data which was stored previously, so that the next output data is stored in the next buffer region of the D/A board before output of the control command signals is completed, and the information processing device may carry out the processing of controlling the D/A board, for each of the plural testing units and by multitasking control, such that the control command signals are outputted continuously. Because the storing of the output data is thereby completed in a short time period, the control command signals can be outputted continuously to the respective testing units.

Moreover, in the above-described structure, the information processing device may further carry out automatic restarting control processing which automatically restarts output of the control command signals, when output of the control command signals by the D/A board is stopped. In this way, even in the unlikely event in which output of the control command signals stops, restoring can be carried out automatically, and the testing system can be normally operated over a long period of time and very stably.

The information processing device relating to the above-described aspect may be provided with interface identifying variables, which are for identifying the testing unit which is the object of instruction in a case in which an operator gives instructions with respect to any of the plurality of testing units by the interface processing, and control identifying variables, which are different from the interface identifying variables and which are for identifying the plurality of testing units used in the feedback control processing, the control processing at the time of an abnormality, and automatic data storing processing which automatically stores data during testing. In this way, confusing of the testing units between processing which operates the plural testing units automatically by multitasking control, and processing which is instructed by the operator, is eliminated, and erroneous operation at the multiple testing system can be prevented.

The control identifying variables may be local variables which are effective only in processings in which the control identifying variables are used. In this way, even if another processing interrupts and is executed by multitasking control, confusing of the testing units is eliminated, and erroneous operation of the multiple testing system can be prevented. Further, the interface identifying variables may be global variables which are effective in all processings which the operator instructs. In this way, the testing unit, for which the operator instructs processing, is specified, and erroneous operation can be prevented.

The feedback control processing of the information processing device relating to the above-described aspect may, in addition to usual feedback control based on an error between the target value and the load quantity detected by the detector, also effect control by correcting the target value each predetermined time period. Because the target value is corrected by directly reflecting the error in this way, stable and highly-accurate control can be carried out under a broad range of test conditions.

The load quantity relating to the above-described aspect may be temperature, or at least one mechanical quantity among load, displacement or strain.

The interface processing relating to the above-described aspect may be at least one of inputting test conditions, instructing start of testing, confirming intermediate progress of testing, confirming an operating status of the system, instructing ending of testing, processing relating to mounting of the test body, processing relating to removal of the test body, or storing test data.

The abnormality of the test body relating to the above-described aspect may be a fracture of the test body, generation of cracks at the test body or a degradation of rigidity of the test body. Further, the abnormality of the testing unit relating to the above-described aspect may be an abnormality of the load quantity applied by the loading mechanism. Moreover, the power source of the loading mechanism relating to the above-described aspect may be a hydraulic power source, and the abnormality of the power source may be an abnormality in hydraulic pressure or oil temperature.

In accordance with a second aspect of the present invention, there is provided a testing method by a multiple testing system having: a plurality of testing units which are disposed independently and each have a frame, a loading mechanism supported at the frame and loading a desired load quantity on a test body, and a detector detecting a load quantity applied on the test body; and a single information processing device carrying out processings with respect to the plurality of test bodies, the method including: carrying out, by multitasking control by the information processing device and with respect to the plurality of testing units: feedback control processing for, on the basis of the load quantity detected by the detector, controlling the loading mechanism such that the detected load quantity becomes a predetermined target value; control processing at an abnormal time when at least one of an abnormality of the test body, an abnormality of the testing unit, or an abnormality of a power source of the loading mechanism, is detected; and interface processing with an operator.

As described above, in accordance with the multiple testing system and testing method of the above-described aspects, by carrying out testing simultaneously by plural testing units, the time required for testing can be shortened, and, even if there are multiple testing units, all of the testing units can continue testing stably over a long period of time. Further, by providing the single information processing device and using it in common at the plural testing units, costs required for the multiple testing system can be suppressed.

What is claimed is:

1. A multiple testing system comprising:
   a plurality of testing units which are disposed independently and each have a loading mechanism applying a desired load quantity on a test body, and a detector detecting a load quantity applied on the test body;
   a single information processing device which includes a feedback control and, by multitasking control and with respect to the plurality of testing units, carries out test processing which includes: feedback control processing for, on the basis of the load quantity detected by the detector, controlling the loading mechanism such that the detected load quantity becomes a predetermined target value; control processing at an abnormal situation when at least one of an abnormality of the test body, an abnormality of a testing unit of the plurality of testing units, or an abnormality of a power source of the loading mechanism, is detected; and interface processing with an operator, wherein each of the plurality of test units is associated with a predetermined target value, and the single information processing device controls the predetermined target value of each of the plurality of testing units independently; and
   means for carrying out a constant value control, in the control processing at an abnormal situation when an abnormality of the test body of one of the testing units is detected, by changing the target value with respect to the one of the testing units to a predetermined constant value while the operation of the other testing units continues as is.

2. The multiple testing system of claim 1, wherein the respective loading mechanisms of the plurality of testing units are connected in parallel to the single power source.

3. The multiple testing system of claim 1, wherein the control processing of the information processing device at an abnormal situation effects constant value control by changing the target value to a fixed value which is determined in advance for each cause of abnormality, when at least one of the abnormality of the test body, the abnormality of the testing unit, or the an abnormality of the power source of the loading mechanism is detected.

4. The multiple testing system of claim 1, wherein the loading mechanism applies one or more of a desired load, displacement, strain, or temperature on the test body, the feedback control has one or more control modes among a displacement controlling mode which controls displacement of the test body, a load controlling mode which controls a load applied on the test body, a load—displacement combination controlling mode simultaneously controlling the load and the displacement, a strain controlling mode controlling strain caused in the test body, a temperature controlling mode controlling the temperature, or a temperature—mechanical quantity combination controlling mode simultaneously controlling temperature and any of load, displacement or strain, and since mounting the test body on any one of the testing units until removal of the test bodies from all of the testing units, control is carried out in accordance with a same controlling mode without switching the controlling mode.

5. The multiple testing system of claim 1, wherein the information processing device further carries out replacement processing which effects control by changing the target value, at a time of removing the test body and at a time of mounting the test body.

6. The multiple testing system of claim 1, wherein the information processing device further has a multichannel D/A (Digital-Analog converter) board which outputs control command signals for controlling the loading mechanisms to the respective plurality of testing units, the D/A board has a plurality of buffer regions storing output data expressing the control command signals, and has a function of continuously outputting of the control command signals by repeating a series of operations of, when the D/A board outputs a predetermined amount of the control command signals, the D/A board sends an event signal requesting next output data, and, before output of output data stored in an active buffer region previously is completed, the D/A board stores the next output data in a next buffer region, and the D/A board further has a function of outputting a constant control command signal and maintaining it, in a case in which the next output data is not stored in the next buffer region when output of the control command signals has been completed.

7. The multiple testing system of claim 6, wherein the information processing device continuously outputs the control command signals by controlling such that a sum of a time period t2, which is required for storage of the next output data, and a time period t3, which is required for a processing whose required time is longest among processings which are carried out continuously and cannot sense the event signal, is shorter than a time period t1, which is since the event signal is sent from the D/A board until completion of the output of the control command signals expressed by the output data which was stored previously, so that the next output data is stored in the next buffer region of the D/A board before output of the control command signals is completed.

8. The multiple testing system of claim 7, wherein the information processing device further carries out automatic restarting control processing which automatically restarts output of the control command signals, when output of the control command signals by the D/A board is stopped.

9. The multiple testing system of claim 1, wherein the information processing device is provided with an interface identifying variable and control identifying variables, the interface identifying variable is a global variable which is effective in all processings which the operator instructs, values of the interface identifying variable being changed only when the operator carries out input which intentionally changes from one testing unit to another testing unit that the operator instructs in the interface processing, wherein a change of the values of the interface identifying variable is not carried out automatically, the control identifying variables are local variables which are effective only in processings in which the control identifying variables are used, in a case in which the operator gives instructions with respect to any of the plurality of testing units by the interface processing, wherein even if another processing is carried out by an interruption processing executed by multitasking control, confusion of the testing units between processing which operates the plurality of testing units automatically by multitasking control, and processing which is executed automatically by the interruption processing, is eliminated, the interface processing is carried out by identifying the one of the testing unit which is an object of instructions in accordance with the interface identifying variable, and the feedback control processing is carried out by identifying the plurality of testing units that is a target of the feedback control in accordance with the control identifying variables, thereby confusion of the testing units between processing which operates the plurality of testing units automatically by multitasking control, and processing which is instructed by the operator, is eliminated.

10. The multiple testing system of claim 1, wherein, in addition to usual feedback control based on an error between the target value and the load quantity detected by the detector, the feedback control processing of the information processing device also controls by correcting the target value each predetermined time period.

11. The multiple testing system of claim 1, wherein the load quantity is temperature, or at least one mechanical quantity among load, displacement or strain.

12. The multiple testing system of claim 1, wherein the interface processing is at least one of inputting test conditions, instructing start of testing, confirming intermediate progress of testing, confirming an operating status of the system, instructing ending of testing, processing relating to mounting of the test body, processing relating to removal of the test body, or storing test data.

13. The multiple testing system of claim 1, wherein the abnormality of the test body is a break of the test body, generation of cracks in the test body or degradation of rigidity of the test body.

14. The multiple testing system of claim 1, wherein the abnormality of the testing unit is an abnormality of the load quantity applied by the loading mechanism.

15. The multiple testing system of claim 1, wherein the power source of the loading mechanism is a hydraulic power source, and the abnormality of the power source is an abnormality in hydraulic pressure or oil temperature.

16. A testing method by a multiple testing system comprising: a plurality of testing units which are disposed independently and each have a loading mechanism applying a desired load quantity on a test body, and a detector detecting a load quantity loaded on the test body; and a single information processing device carrying out processings with respect to the plurality of test bodies, the method comprising:

carrying out, by multitasking control by the information processing device and with respect to the plurality of testing units, test processing which includes:

feedback control processing for, on the basis of the load quantity detected by the detector, controlling the loading mechanism such that the detected load quantity becomes a predetermined target value;

control processing at an abnormal situation when at least one of an abnormality of the test body, an abnormality of a testing unit of the plurality of the testing units, or an abnormality of a power source of the loading mechanism, is detected; and interface processing with an operator; and carrying out a constant value control, in the control processing at an abnormal situation when an abnormality of the test body of one of the testing units is detected, by changing the target value with respect to the one of the testing units to a predetermined constant value while the operation of the other testing units continues as is, wherein each of the plurality of test units is associated with a predetermined target value, and the single information processing device controls the predetermined target value of each of the plurality of testing units independently.

17. A multiple testing system comprising:

a plurality of testing units which are disposed independently and each have a loading mechanism applying a desired load quantity on a test body, and a detector detecting a load quantity applied on the test body;

a single information processing device which includes a feedback control and, by multitasking control and with respect to the plurality of testing units, carries out test processing which includes: feedback control processing for, on the basis of the load quantity detected by the detector, controlling the loading mechanism such that the detected load quantity becomes a predetermined target value; control processing at an abnormal situation when at least one of an abnormality of the test body, an abnormality of a testing unit of the plurality of testing units, or an abnormality of a power source of the loading mechanism, is detected; and interface processing with an operator; and means for carrying out a constant value control, in the control processing at an abnormal situation when an abnormality of the test body of one of the testing units is detected, by changing the target value with respect to the one of the testing units to a predetermined constant value while the operation of the other testing units continues as is, the predetermined constant value being smaller than a residual strength of the test body.

18. A testing method by a multiple testing system comprising: a plurality of testing units which are disposed independently and each have a loading mechanism applying a desired load quantity on a test body, and a detector detecting a load quantity loaded on the test body; and a single information processing device carrying out processings with respect to the plurality of test bodies, the method comprising:

carrying out, by multitasking control by the information processing device and with respect to the plurality of testing units, test processing which includes:

feedback control processing for, on the basis of the load quantity detected by the detector, controlling the loading mechanism such that the detected load quantity becomes a predetermined target value;

control processing at an abnormal situation when at least one of an abnormality of the test body, an abnormality of a testing unit of the plurality of the testing units, or an abnormality of a power source of the loading mechanism, is detected; and interface processing with an operator; and carrying out a constant value control, in the control processing at an abnormal situation when an abnormality of the test body of one of the testing units is detected, by changing the target value with respect to the one of the testing units to a predetermined constant value while the operation of the other testing units continues as is, the predetermined constant value being smaller than a residual strength of the test body.

* * * * *

UNITED STATES PATENT AND TRADEMARK OFFICE
CERTIFICATE OF CORRECTION

| | |
|---|---|
| PATENT NO. | : 7,975,557 B2 |
| APPLICATION NO. | : 11/655073 |
| DATED | : July 12, 2011 |
| INVENTOR(S) | : Hiroshi Hohjo et al. |

It is certified that error appears in the above-identified patent and that said Letters Patent is hereby corrected as shown below:

Column 19, line 4, please delete "or the an abnormality" and replace with --or the abnormality--

Column 20, line 44, please delete the following "the target value each" and replace with --the target value in each--

Signed and Sealed this
Thirteenth Day of September, 2011

David J. Kappos
*Director of the United States Patent and Trademark Office*